US006770288B2

(12) United States Patent
Duirs (10) Patent No.: US 6,770,288 B2
(45) Date of Patent: Aug. 3, 2004

(54) DRUG DELIVERY SYSTEM

(75) Inventor: Graham Francois Duirs, Hamilton (NZ)

(73) Assignee: Pfizer Products Inc., Groton, CT (US)

( * ) Notice: Subject to any disclaimer, the term of this patent is extended or adjusted under 35 U.S.C. 154(b) by 0 days.

(21) Appl. No.: 09/622,094

(22) PCT Filed: Feb. 9, 1999

(86) PCT No.: PCT/NZ99/00016

§ 371 (c)(1),
(2), (4) Date: Oct. 17, 2000

(87) PCT Pub. No.: WO99/40966

PCT Pub. Date: Aug. 19, 1999

(65) Prior Publication Data

US 2003/0039679 A1 Feb. 27, 2003

(30) Foreign Application Priority Data

Feb. 13, 1998 (NZ) ................................................ 329799
Nov. 13, 1998 (NZ) ................................................ 332795

(51) Int. Cl.[7] ................................................ A61F 13/00
(52) U.S. Cl. ...................................... 424/422; 424/438
(58) Field of Search ............................... 424/422, 438; 128/260, 268, 830

(56) References Cited

U.S. PATENT DOCUMENTS

| 2,127,094 | A |   | 8/1938  | Strauss  | 128/269 |
| 2,170,222 | A |   | 8/1939  | Strauss  | 128/269 |
| 3,818,911 | A | * | 6/1974  | Fournier | 128/269 |
| 3,920,805 | A |   | 11/1975 | Roseman  | 424/15  |
| 3,995,633 | A |   | 12/1976 | Gougeon  |         |
| 4,988,512 | A |   | 1/1991  | Azria    |         |
| 5,840,055 | A |   | 11/1998 | Sgro     | 604/11  |

FOREIGN PATENT DOCUMENTS

| CH | 688 984 A5   | 7/1998 |
| GB | 2 154 875 A  | 9/1985 |
| WO | WO 81/00356  | 2/1981 |
| WO | WO 93/15788  | 8/1993 |
| WO | WO96/15724   | 5/1996 |
| WO | WO 97/15242  | 5/1997 |

OTHER PUBLICATIONS

European Search Report, Appl. No. 99 90 5381.

* cited by examiner

Primary Examiner—Thurman K. Page
Assistant Examiner—Konata M. George
(74) Attorney, Agent, or Firm—Finnegan, Henderson, Farabow, Garrett & Dunner, LLP

(57) ABSTRACT

A drug delivery device for delivering hormonal and other veterinary treatments intra-vaginally. A substance dispenser (21) is separate from the supporting device (20). The dispenser is in the form of drug impregnated gills or vanes (6, 7). In other aspects the drug may be dispensed by a micropump in the supporting device or the drug may be coated on the dispenser.

19 Claims, 6 Drawing Sheets

DRUG DELIVERY SYSTEM

TECHNICAL FIELD

This invention relates to a substance delivery system.

Reference throughout the specification shall be made to the use of the present invention as a drug delivery system for use in animal body cavities, such as the vagina.

It should be appreciated however that the present invention can be used to deliver substances other than drugs and can be used in relation to humans and in other body cavities, for example the rumen, ears and so forth.

BACKGROUND ART

Drug delivery systems are used extensively in controlled breeding and reproductive management. Although considerable research has been invested in the design of these devices, there are still problems associated with them.

Firstly, these devices are required to be retained within the body cavity for the slow release of drugs over a period of time. To facilitate this, various arms and projections have been built into the device which can either engage with the walls of the body cavity, or make the device wide enough such that when in the body cavity it cannot naturally exit the animal through the entrance orifice.

Major problems with the provision of such arms or projections is that they can irritate or even rupture the lining of the body cavity, causing distress to the animal and providing a site for possible infection.

A major problem with drug delivery devices is that traditionally they have been manufactured with the drug impregnated into the material from which the device is made. Typically, this material is in many instances a matrix of silicone.

To manufacture devices from drug impregnated silicone is expensive.

A further disadvantage of using a drug impregnated device is that it is very difficult to dispose. For example, the hormones used in reproductive management are required to be disposed in accordance with heavily regulated environmental procedures. As it is always possible that the drug within the silicone matrix had not been fully delivered to the animal when the device is removed, the whole device will have to be disposed as the whole device is the drug delivery system.

It would be desirable if the devices could be reused.

Another problem with the devices is that they have a specific dose rate which cannot be readily changed. Further with these devices, the treatment cannot be changed or customised according to requirements.

In some animals such as cows, the progesterone dose rate for synchronising oestrus is critical to the reproductive cycle. Typically, in the pre-luteal phase the animal will reproduce follicles which are the stage that ovum are produced. Follicule maturation then occurs and the follicule develops into the corpus luteum in the ovary. Fertilisation can then occur.

Therefore healthy follicules are a pre-requisite for conception.

Exogenous progesterone is often delivered to cows to inhibit follicle maturation as a means of synchronising oestrus. When the treatment is removed progesterone levels fall and the animals cycle in a controlled manner. If however the progesterone blood levels during treatment fall below critical levels oestrus synchronisation may still occur but follicle integrity may be compromised thereby reducing conception rates and fertility. This condition highlights the necessity to maintain adequate progesterone dose using an efficient drug delivery system.

To maintain adequate dose previous drug delivery systems have contained excessively high progresterone dose levels. This has resulted in high residual levels of drug remaining in the device after use which has adverse economic and environmental impacts.

In addition, various applications of a treatment may require different drug delivery periods. For instance, one treatment may require six days drug delivery, another treatment may require ten days drug delivery. In this situation an ability to offer dose choice would be feasible. Also, very large animals of the European breeds may require larger doses than the smaller animals on pastoral systems in countries like New Zealand.

What would be desirable then is a drug delivery device that delivers the drug in a sufficient quantity over the treatment period with a minimum of residual drug remaining in the device matrix after treatment to achieve production economies and to avoid adverse environmental impacts caused by disposing used devices in land fills that contain large quantities of hormones. Flexibility in being able to change or customise the treatment would be desirable.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a substance delivery device,
  including a substance dispenser
  characterised in that the surface area of the substance dispenser is independent of the supporting structure of the substance delivery device.

The substance delivery device should now be referred to as a drug delivery device such as an intravaginal release device (IRD).

It should be appreciated however that a device in accordance with the present invention can be adapted for use in other body cavities such as the rumen, the auditory system, the gum area and other body cavities.

It should also be appreciated that the present invention can be used in both humans and animals.

In preferred embodiments, the present invention may be used in the treatment of cows.

The applicant has recognised that a dissolution process as a means of drug delivery is very effective provided the drug release process is controlled. The applicant has in his invention concentrated on the principles which aid dissolution, namely the surface area and thinness of the substance dispensers, surface area exposed directly to the body cavity and in some embodiments the holding of drugs in cavities in the dispenser.

It should be appreciated however that other drug delivery methods can be used such as mechanical or electronic.

The present invention can also be used to introduce a biological monitor such as a thermometer.

As a further issue the applicant has also been conscious of providing a ready means by which the drug profile delivered by the substance delivery device can be readily modified.

For example, different animal weights require different amounts of drugs.

The substance being delivered may come in a variety of forms. For example, these may be liquid, bullets, powder, gel, and other such forms. However, this list should not be seen to be exhaustive.

In one embodiment, the substance dispenser may be a pod with a housing containing vanes. Preferably, the pod may take the form of an obloid. The vanes may be positioned so that they are axially directed through the centre of the sphere and are in contact with the inside of the sphere at their outer edges.

Having one embodiment of the substance dispenser as a pod should not be seen to be limiting, as the principles of the present invention may be applied using a substance dispenser of a different configuration.

For example the substance dispenser may be a substantially cylindrical device containing vanes, or containing a grid, honeycomb or mesh arrangement. The grid, honeycomb or mesh arrangement may also be applied to the pod configuration for equal effectiveness.

In preferred embodiments, the dispenser may be a temporary attachment to a supporting structure, or could be applied as a permanent attachment to a supporting structure. In a further preferred one embodiment the dispenser may be a free-standing delivery pod within the body cavity.

Preferably the dispenser may be used as a temporary attachment to a supporting structure, such as can be found in New Zealand Patent Application No. 328967. Reference to the device in New Zealand Patent No. 328967 should not be seen to be limiting, as the supporting structure may constitute another form of device while still maintaining the advantages of the dispenser.

In some embodiments in the present invention the dispenser may be used in conjunction with existing structures on the market such as those described in New Zealand Patent No. 207341. The substance delivery device disclosed in that patent application has substance to be delivered contained in the matrix of the supporting structure with all of the inherent problems described earlier in this patent specification. However, the present invention could be used to provide add-on substance delivery devices to its supporting structure which may either supplement or substitute for the substance contained within that supporting structure.

One advantage of configuring the dispenser as a pod containing vanes is that the pod has a large surface area, provides increased durability, and provides increased comfort to the animal to which the device is applied.

In further preferred embodiments, the dispenser may have the capability of having supplementary dispensers attached to an existing dispenser. These supplementary dispensers may be of any suitable shape, such as a cylindrical device, a grid arrangement or a honey-comb or mesh arrangement.

However preferably, the supplementary dispenser may be a substantially cylindrical device containing vanes extending towards the centre of the cylinder.

The above configuration of the supplementary dispenser is that this device may be co-operatively attached to the main dispenser, with greater co-operation between the two structures, due to the facing edges of the two dispensers being substantially the same configuration.

The advantage of a supplementary dispenser as discussed above will be discussed further on.

In preferred embodiments the support structure may be any device that maintains the structural rigidity of the substance delivery device. For example the support structure may be a frame, a system of struts, a cantilever support, an air cushion support, a hydraulically supported device, or some other means of support.

In preferred embodiments, the substance being delivered may be drugs such as hormone treatment substances, for example, progesterone. Reference to the substance being delivered shall hereafter be referred to as drugs, however this should not be seen to be limiting the scope of the present invention's manufacture or use, as other substances may be delivered by the present invention without departing from the present invention's scope of manufacture or use.

This should not be seen to be limiting as other drug delivery devices may be used.

For example, the drug delivery device may be a spine (support structure) with fingers or objects extending from the centre of the spine that carry the drug and such fingers or objects.

Alternatively, there may be a central fixture point with radially extending arms or fingers. The substance to be delivered may be coated or impregnated on these spines or fingers.

Other embodiments of the present invention may be used without departing from the scope of the present invention.

Preferably, the vanes may be coated or impregnated with the substance to be dispensed. This has a number of advantages.

The increased surface area of the IRD means that a greater rate of substance transfer may be achieved. Furthermore, the relatively thin nature of the vanes means that a substance that is contained within the material the vanes consist of, may diffuse more quickly to the outside surface of the vane and be transferred to the animal. This means that a greater proportion of the drugs will be dispensed.

The ability to regulate the device surface area to influence dose levels and to regulate the dose profile through matrix thickness enables specific dose formulations to be delivered through design by varying vane sizes and thickness.

Therefore, the problems associated with residual progesterone in the device may be reduced or overcome. Reduced thickness of the vanes coupled with increased surface area creates more efficient drug transfer resulting in reduced residue. No drugs are associated with the support structure of the IRD.

Therefore, maximum release of drug to specific dose requirements is achieved also providing minimal residue and an ability to modify surface areas and matrix thickness to meet specific treatment needs. With progesterone treatment good synchrony and fertility rates may be achieved using considerably less progesterone and matrix raw material than existing technologies. Drug residue will be considerably less than existing technologies.

In further preferred embodiments, the vanes may be coated with different drugs and different combinations. This has an advantage that a multi drug dosing system may be implemented.

In some embodiments, the vanes may be configured so that they form a cavity within the drug delivery device. This has a number of advantages.

The first advantage is that the cavities provide an increased surface area whereby fluid which is body fluid may interact with the increased surface area in the cavity, thereby increasing the capacity for the device to dispense the particular drug desired.

Secondly the cavities provide a space whereby additional materials such as further drugs may be stored for release, improving the drug dispensing economy and storage capacity of the drug dispensing device.

A third advantage of the cavities is that a greater number of cavities provides for multi-dose variability within specific cavities, for delivery of various drug delivery profiles. Thus depending on the dosing required, the amount of drug and particular type of drug may be stored in a particular cavity.

The vanes or cavity surface may be covered with a biodegradable surface to rate release additional substance.

By combining various drugs with various vane thicknesses, the consumer may tailor the drug delivery and dosing to match the particular need of the animal. These needs may be in terms of a type of drug required to be dispensed, and the length of time the drug should be dispensed in.

Thus, various drug delivery profiles may be achieved.

In preferred embodiments, the vanes may not be surrounded by an outer wall and project directly into the body cavity—being directly exposed to the body fluids in which the drugs dissolve.

Thus the most appropriate dose may be selected and applied to each specific treatment, independent of the main carrier body. This may be selected on the basis of different dosing sizes for larger or smaller animals by weight, but other factors such as the age of the animal, and the medical condition of the animal or other conditions may be used.

The present invention may be manufactured from any substance capable of being impregnated or coated with, and then releasing a drug. For example the present invention may be manufactured from plastic, kevlar™, wood, glass, silicone or other substances.

Preferably however, the present invention may be manufactured from plastics material, polymers or elastomers. The advantages this gives are that the plastic is easily manufactured into the desired shape, is cheap to manufacture, and is malleable so as to prevent irritation to the animal when in use.

In preferred embodiments the material from which the substance dispenser is biomedical silicone elastomer rubber (polydimethylsiloxane). The applicant has found that this material is soft, pliable, does not irritate body tissues and can carry release substances embedded in its matrix.

The feature of the present invention regarding the supplementary dispenser, enables increased control over dose variance. A supplementary dose or a half dose or other dose profiles may be applied by fixing a supplementary dispenser to the main carrier body or to the existing dispenser.

Thus, more than one substance may be delivered at a time.

The use of a dispenser provides the ability to replenish treatments or applications, and/or apply them for sustained periods by replacing the dispenser, or adding a supplementary dispenser.

The dispenser design maximises the surface area such that the dose can be enhanced. This is particularly useful when silicone or polymer type materials are used in the construction of the dispenser for delivering the substances via dissolution processes.

The thickness of the vanes can be modified and varied such that the drug delivery rates can be manipulated to suit the species and dose profiles required.

An example of the benefits of a dispenser application follows.

In the intravaginal delivery of progesterone in cattle, whereby progesterone is impregnated into a silicone matrix requiring a sustained dose of approximately two ng/ml of exogenous progesterone in the blood. If dose levels decline below this, the follicule condition is impaired and the desired conception rates from the treatment are not achieved after removal of the device.

Using the dispenser, various forms of drug delivery can be applied and are not limited to polymer-based dissolution systems. For example, the dispenser cavities could be loaded with substances using a biodegradable coating to regulate the release.

Alternatively an electronically controlled pump may be inserted in the dispenser to release the substance.

In a further preferred embodiment, biological monitor such as an electronic thermometer may be inserted into at least one dispenser to provide real time body temperatures. Alternatively, monitors to detect pH, trace elements, hormones, bateria or viruses may be used.

This has an advantage when determining and monitoring an animal's bodily functions, which may be used to determine the dose variants or drug delivery profile required.

In preferred embodiments, the substance dispenser is in the form of drug impregnated gills attached to the supporting structure. The surface area of the gills can control the amount of drug delivered and the thickness and number of the gills controls the duration of the dose, and the dose profile.

Surface area based on flaps or gills that have no "central spine" component (as in CIDR patent) provides a pliable matrix and enables protruding shapes such as gills to be used as these can be compacted for insertion into the body cavity and do not irritate mucosa due to their softness and shape. The lack of a rigid spine component also reduces the overall mass of the device.

Therefore, the size of the gills can be used to modify the drug profile as required. Preferably, the profile has a fast drop off with little residual drugs as a consequence of applying these novel design concepts.

The gills may also be impregnated with different drugs.

In some embodiments, the gills may be of different types, for example, end gills and middle gills, wherein the end gills ensure the middle gills are secured with respect to the supporting structure.

The gills have a central aperture that allows them to be readily pushed onto (or pulled off) a supporting structure. This allows the number of gills and hence dosage amount to be readily changed. Also, only one supporting structure can be used for multiple treatments by removing expended gills and replacing them with fresh gills.

This leads to significantly less wastage than previous devices and less disposal problems.

In a preferred embodiment of the present invention, the gills are moulded into a sleeve which slides over an arm of the supporting structure. By having the gills moulded into the sleeve, the spacing between the gills can be optimised to ensure that there is no competition between the gills in terms of drug release and that the mucosal absorption is not overloaded.

In this latest embodiment, the dosage or treatments can be changed by removal of the whole sleeve in replacement of a further one.

The sleeves may also be made with varying numbers of gills depending on the type or amount of treatment which is required to be given.

Preferably, the gills are made of a soft and pliable silicone. This aids animal comfort and welfare and in insertion and removal of the IRD with respect to body orifices. This allows certain configurations of IRDs to be compressed to a smaller size than more rigid devices.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
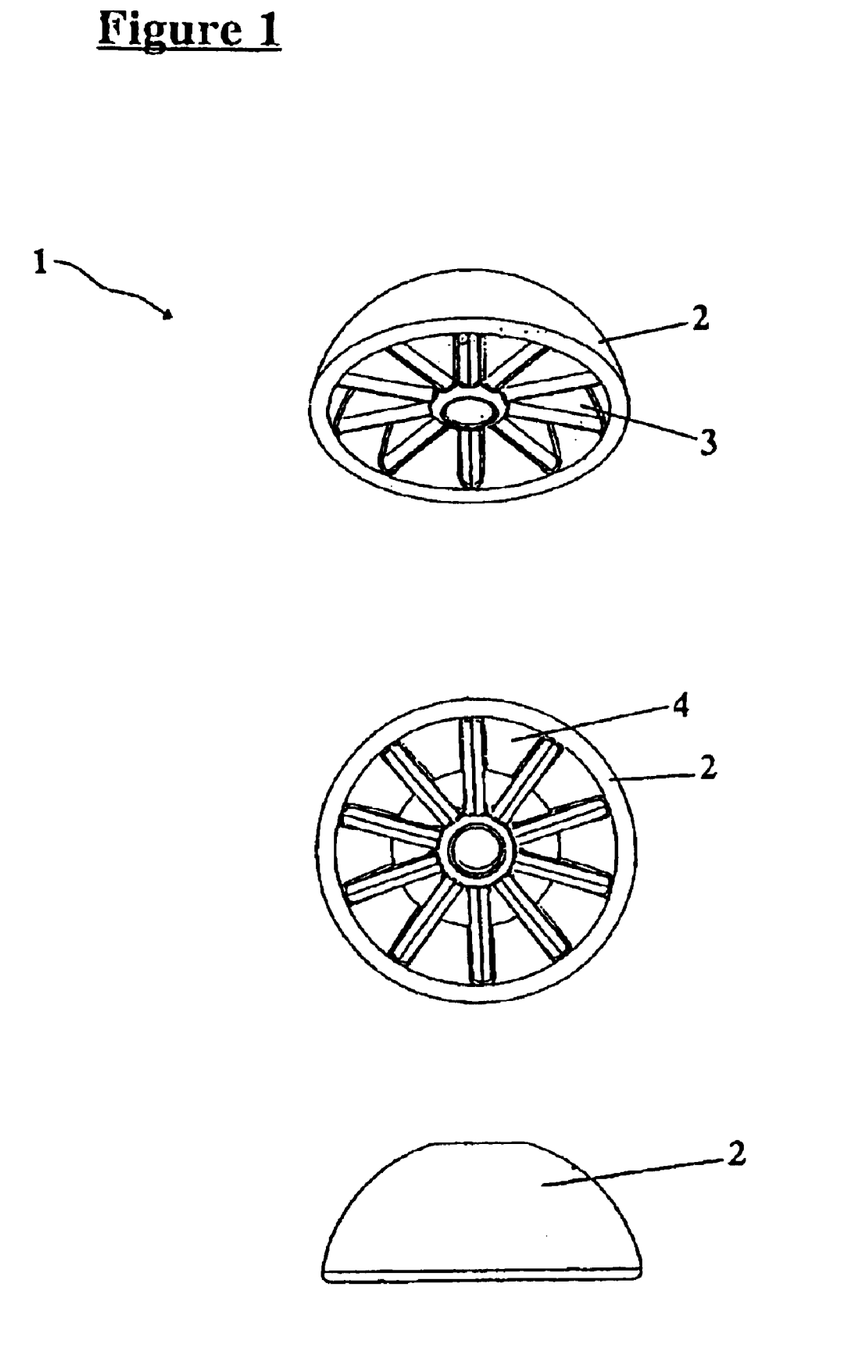
FIG. 1 shows various views of a vaned pod embodiment.

In the reference to FIG. 1 there is shown a plan view of a substance dispenser in the form of a pod generally indicated by arrow 1. The pod includes two half hemispheres (2), supporting vanes (3) and cavities (4).

In use, the pod (1) is attached to a support structure (not shown) before being inserted into the vagina of an animal such as a cow. The hemispheres (2) and the supporting vanes (3) may be coated with the drug that is required to be dispensed. The pod (1) may be fixed to an insertion device not shown.

The supporting vanes (3) may be used as a storage location for further drugs or other substances that are required to be released.

Each of the vanes (3) may be coated or impregnated with the same or a different substance. Similarly, the cavities (4) may hold additional drugs or substances required to be dispensed.

Figure 2:
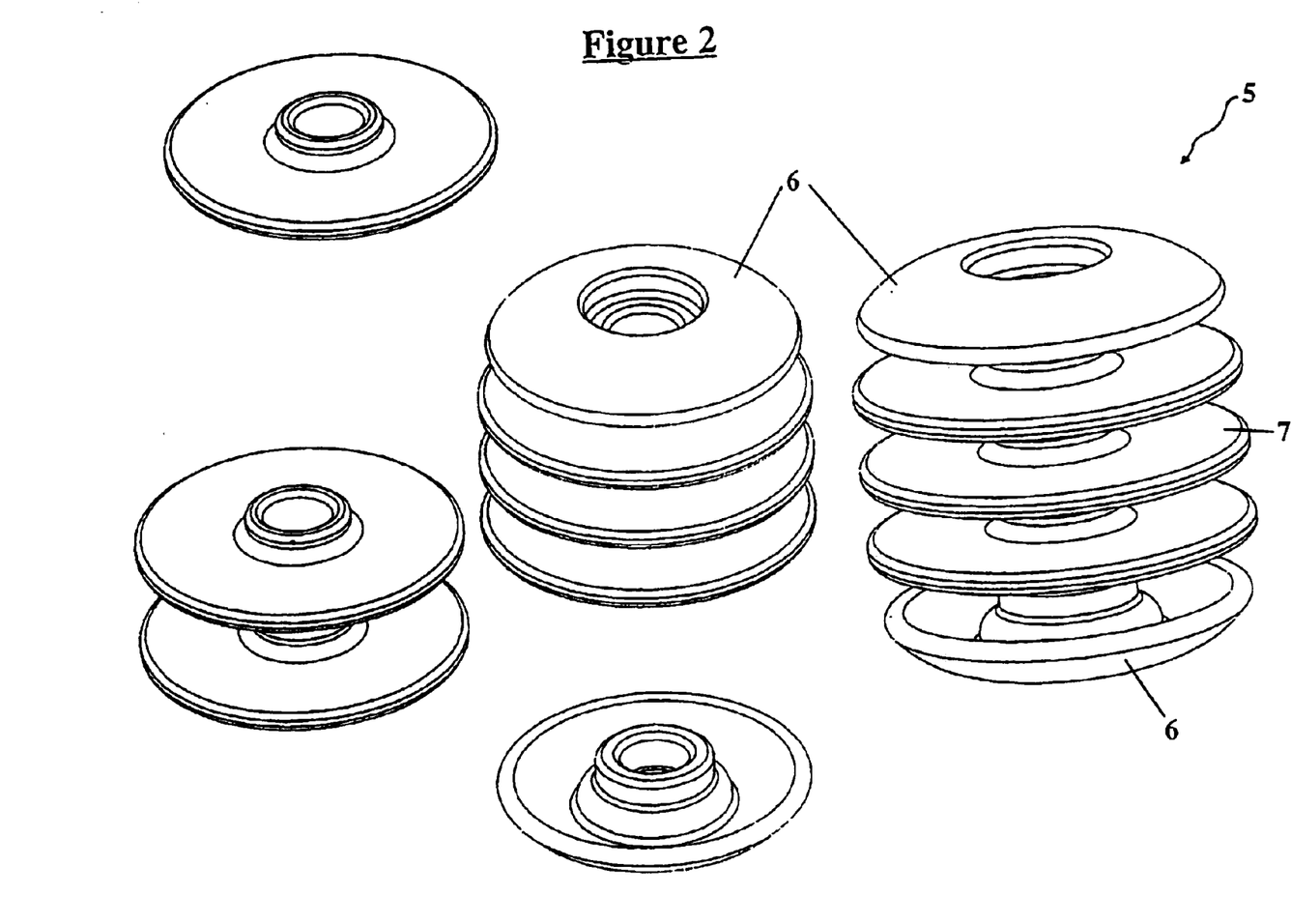
FIG. 2 shows various views of gills used in one embodiments.

FIG. 2 shows individual plates which in combination form gills generally indicated by arrow (5) which can be inserted into a support structure of an IRD.

The end gills (6) can be anchored to the support structure ensuring that the middle gills (7) which may sit loosely on the structure do not fall off.

Figure 3:
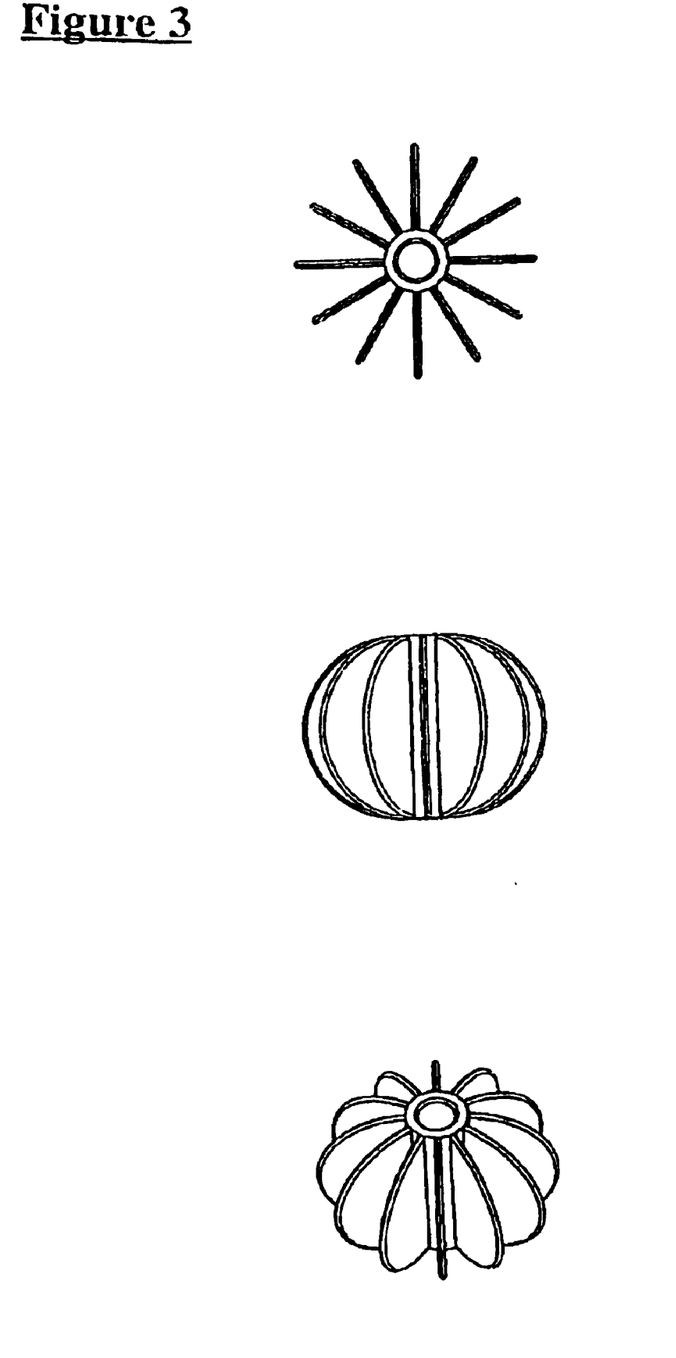
FIG. 3 shows various views of further variation of the pod in FIG. 1.

FIG. 3 illustrates a variation of the embodiment in FIG. 1, without an outer shell allowing the vanes to have direct contact with body fluid.

FIG. 3 illustrates three IRD's, each with the same supporting structure, but with substance dispensers having differing number gills.

Figure 4:
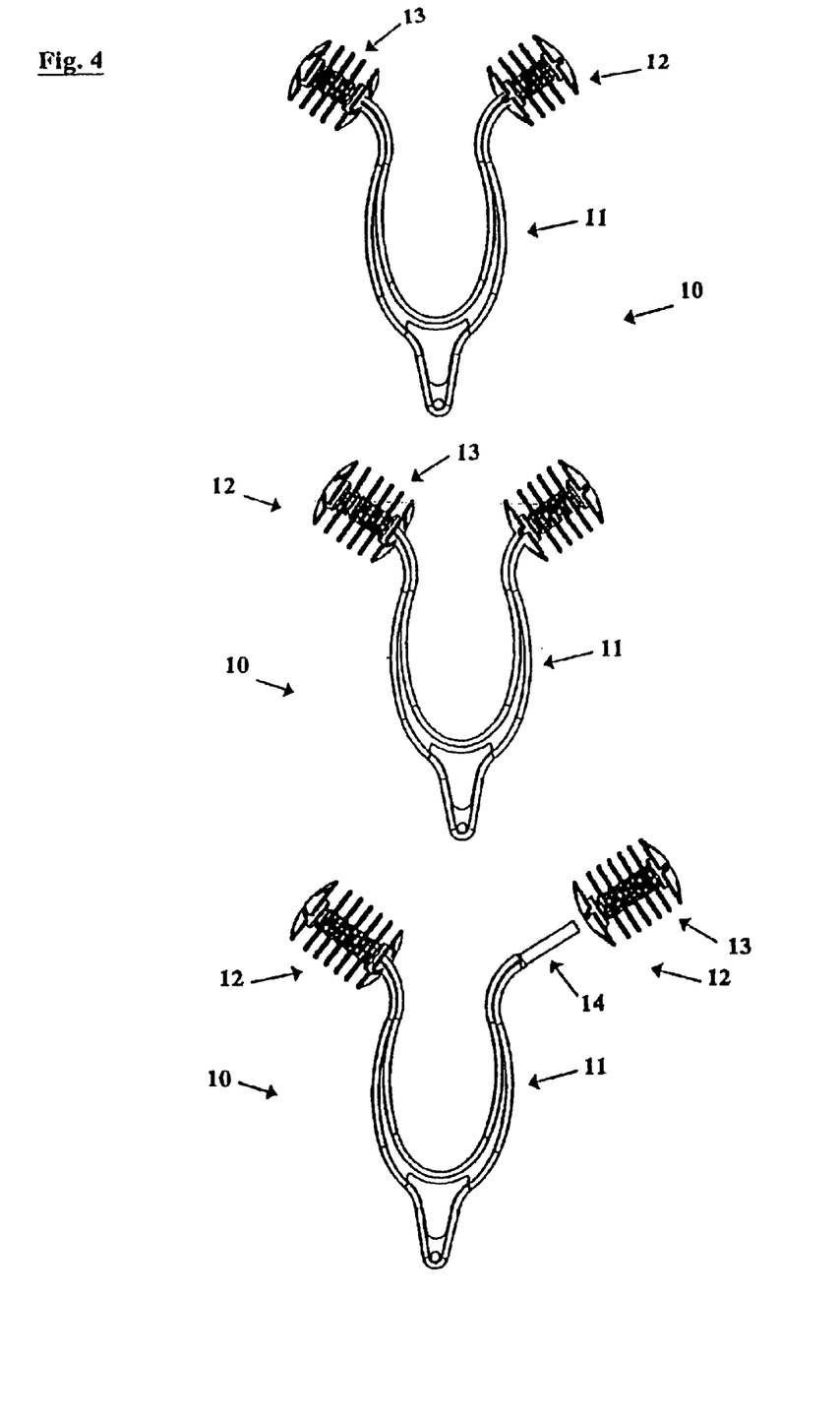
FIG. 4 shows various views of different gill sleeves used in the present invention.

The dispenser (12) in the form of a sleeve having gills (13) moulded therein. Sleeves (12) can be readily fitted over or removed from the arms (14) of the supporting structure (11).

It can be seen that initially different dose amounts can be introduced to the animals by using different sleeves. It should also be seen that after treatment has commenced, there is still flexibility provided through the removal and replacement of the dispensers (12).

Figure 5:
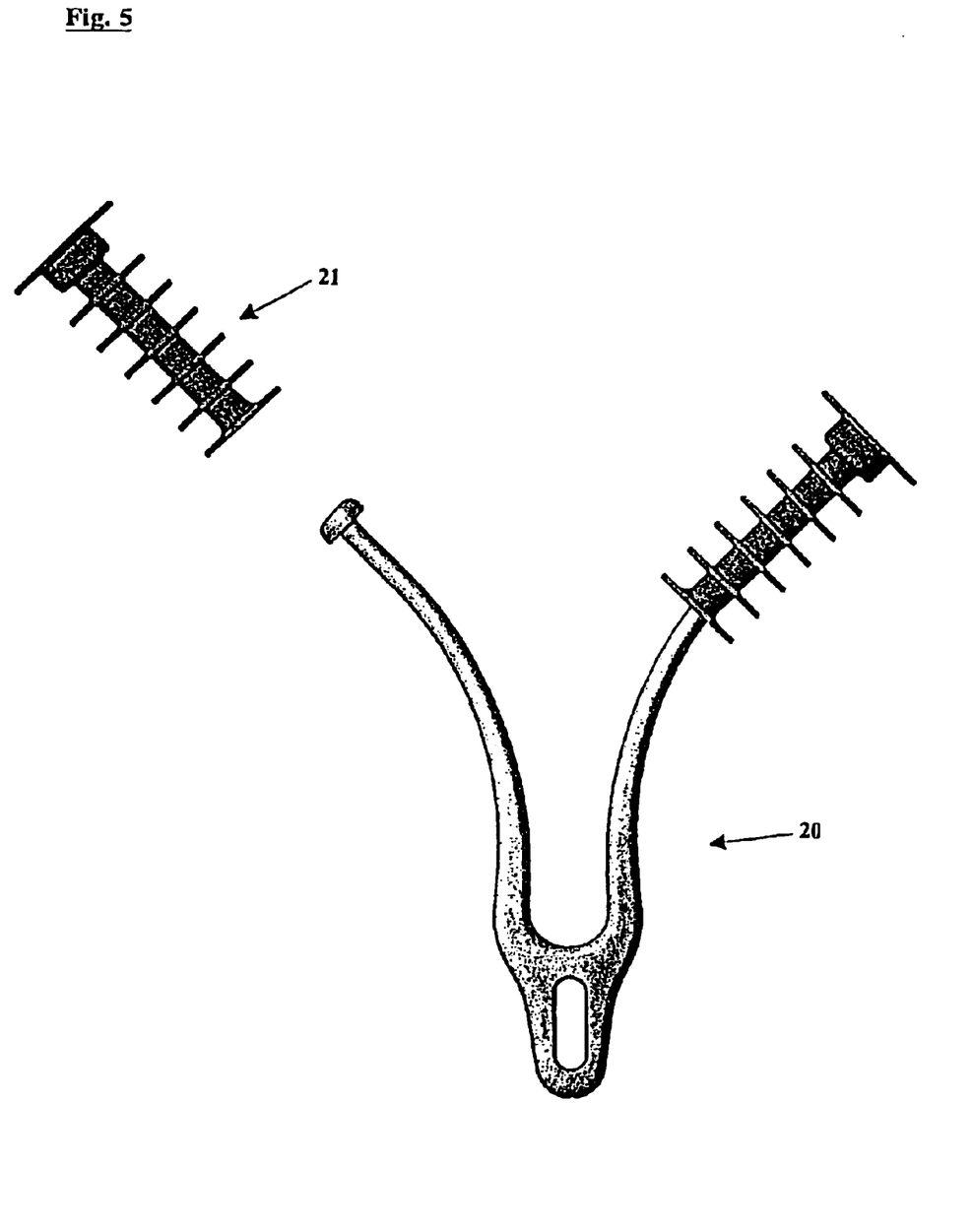
FIG. 5 shows a sleeve embodiment.

FIG. 5 shows an alternate sleeve embodiment of an IRD generally indicated by arrow (20) with a gill sleeve (21) that is detachable.

Consequently, the consumer may design a particular drug delivery profile that is suited to the particular application and needs of the animal. The thickness of the vanes may be varied, to comply with the required dosing rate and drug delivery profile for the particular drug the vanes are impregnated or coated with. Similarly, the cavities in FIG. 1 may contain an appropriate amount of the substance to be delivered, to comply with the particular drug delivery profile required to suit the particular needs of the animal.

Figure 6:
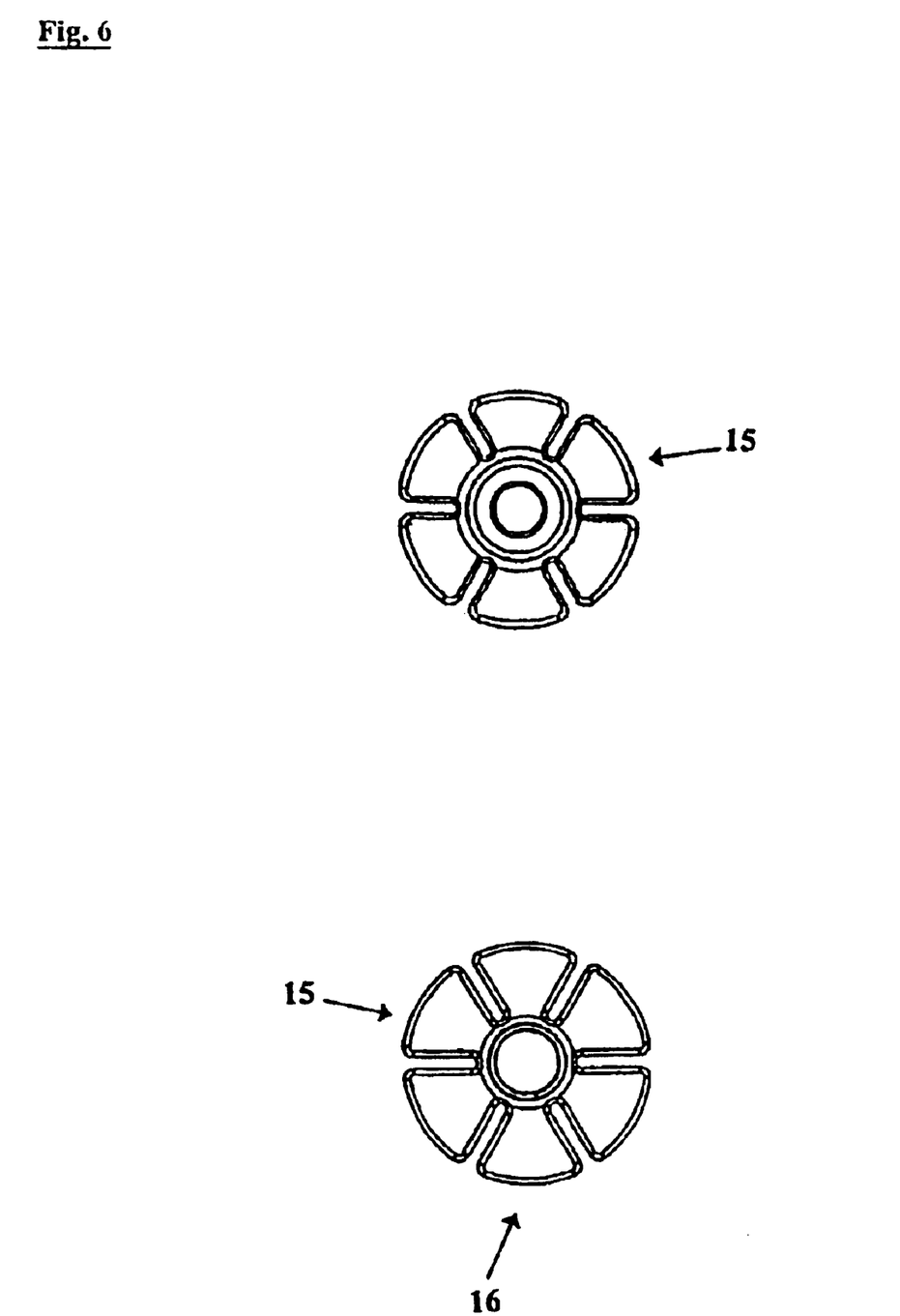
FIG. 6 illustrates a petal shaped variation of the gills.

FIG. 6 illustrates some possible cross-sections of gills (15) in having petals (16). The applicant has found that petals provide greater flexibility/pliability to the gills (15) providing greater animal comfort and ease of insertion as well as enhancing the dissolution process.

Aspects of the present invention have been described by way of example only and it should be appreciated that modifications and additions may be made thereto without departing from the scope of the appended claims.

What is claimed is:

1. A substance delivery device adapted for insertion into a body cavity of an animal, the substance delivery device comprising:

a supporting structure configured to be retained within the body cavity of the animal;

a substance dispenser independent of the supporting structure, the substance dispenser including a plurality of finger means configured to allow sustained release of substances over a period of time, the plurality of finger means radiating from a central aperture; and means for releasably fixing the substance dispenser to the supporting structure so that the central aperture slides over a portion of the support structure, and so that the plurality of fingers extend away from the supporting structure.

2. A substance delivery device as claimed in claim 1 wherein the plurality of finger means are gills.

3. A substance delivery device as claimed in claim 1 wherein the plurality of finger means are vanes.

4. A substance delivery device as claimed in any one of claims 1 to 3 wherein the plurality of finger means are coated or impregnated with the substance to be dispensed.

5. A substance delivery device adapted for insertion into a body cavity, the substance delivery device comprising:

a supporting structure;

a substance dispenser independent of the supporting structure, the substance dispenser including a plurality of finger means for allowing sustained release of substances over a period of time, the plurality of finger means radiating from a central aperture; and means for releasably fixing the substance dispenser to the supporting structure so that the central aperture slides over a portion of the support structure, and so that the plurality of fingers extend away from the supporting structure, wherein the substance dispenser is made from polydimethylsiloxane.

6. A substance delivery device as claimed in any one of claims 1 to 3 wherein the substance dispenser is highly flexible.

7. A substance delivery device as claimed in any one of claims 1 to 3 in the form of an intravaginal release device.

8. A substance delivery device as claimed in any one of claims 1 to 3 configured to be retained within a cow.

9. A substance delivery device adapted for insertion into a body cavity of an animal, the substance delivery device comprising:

a supporting structure;

a substance dispenser independent of the supporting structure the substance dispenser including a plurality of finger means configured to allow sustained release of substances by dissolution over a period of time, the plurality of finger means radiating from a central aperture, wherein the substance dispenser is configured so that substance delivery rate is based upon the thickness of the finger means; and means for releasably fixing the substance dispenser to the supporting structure so that the central aperture slides over a portion of the support structure, and so that the plurality of fingers extend away from the supporting structure.

10. A substance delivery device as claimed in claim 9 wherein the plurality of finger means are gills.

11. A substance delivery device as claimed in claim 10, wherein the gills are configured to be independently removably attached to the supporting structure.

12. A substance delivery device as claimed in claim 11, wherein the gills include end gills and middle gills, the middle gills configured to be retained on the supporting structure by the end gills.

13. A substance delivery device as claimed in claim 11, wherein the gills are moulded so that the central aperture spaces the gills to ensure that there is no competition between the gills in terms of drug release.

14. A substance delivery device as claimed in claim 9, further including a supplementary dispenser releasably fixed to one of the substance dispenser and the supporting structure.

15. A substance delivery device as claimed in claim 9, further including a biological monitor inserted into the substance dispenser.

16. A substance delivery device as claimed in claim 9, wherein the plurality of finger means are vanes.

17. A substance delivery device as claimed in claim 16, wherein vanes are configured to form a cavity within the drug delivery device.

18. A substance delivery device as claimed in claim 16, wherein the vanes are axially aligned with the central aperture.

19. A substance delivery device as claimed in claim 16, wherein the vanes are covered with a biodegradable surface to rate release the substances.

* * * * *